United States Patent [19]

Lesher et al.

[11] 4,331,671
[45] May 25, 1982

[54] 5-(PYRIDINYL)-1H-BENZIMIDAZOLES AND 1-HYDROXY-6-(PYRIDINYL)-1H-BENZIMIDAZOLES AND THEIR CARDIOTONIC USE

[75] Inventors: George V. Lesher, Schodack; Baldev Singh, East Greenbush, both of N.Y.

[73] Assignee: Sterling Drug Inc., New York, N.Y.

[21] Appl. No.: 223,752

[22] Filed: Jan. 9, 1981

[51] Int. Cl.$^3$ .................... A61K 31/44; C07D 401/04; C07D 401/06
[52] U.S. Cl. ..................................... 424/263; 546/271
[58] Field of Search ...................... 546/271; 424/263

[56] References Cited

U.S. PATENT DOCUMENTS 4,026,936 5/1977 Lauer et al. .......................... 424/263
4,188,486 2/1980 Tsukamoto et al. ................. 546/271

OTHER PUBLICATIONS

Zubarovskii et al., Chem. Abst. 141468k, vol. 77, 1972, (Inst. Org. Khim. Kiev, USSR), Khim. Geterotsikl. Soedin 1972, (5), pp. 687–690.
Dol'nikov et al., Chem. Abst., vol. 76, 1972, 135663h.
Wolfgang et al., Chem. Abst., vol. 80, 1974, 95953b.

*Primary Examiner*—Jane T. Fan
*Attorney, Agent, or Firm*—Robert K. Bair; B. Woodrow Wyatt

[57] ABSTRACT

2-R-5-(Py-Y)-1H-benzimidazole or pharmaceutically-acceptable acid-addition salt thereof, useful as a cardiotonic, is prepared by reacting 4-(Py-Y)-1,2-benzenediamine with a tri-(lower-alkyl)ortho-(lower-alkanoate) of the formula R—C(OR$_1$)$_3$, where R is hydrogen or lower-alkyl, Y is a direct linkage or lower-alkylene having one or two carbon atoms, and Py is 4- or 3-pyridinyl or 4- or 3-pyridinyl having one or two lower-alkyl substituents, or with dimethylformamide dimethyl acetal or dimethylacetamide dimethyl acetal to produce said 2-R-5-(Py-Y)-1H-benzimidazole where R is methyl or ethyl respectively. The same compound where R is lower-alkyl is prepared in two steps by first reacting 4-(Py-Y)-1,2-benzenediamine with an alkanoylating agent providing alkanoyl of the formula

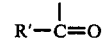

to produce N$_2$—[R'—C(=O)]-4-(Py-Y)-1,2-benzenediamine and heating the latter compound to produce said 2-R'-5-(Py-Y)-1H-benzimidazole, where R' is lower-alkyl. Also shown is 1-hydroxy-2-R-6-(Py-Y)-1H-benzimidazole or pharmaceutically-acceptable acid-addition salt thereof, useful as a cardiotonic and prepared by reacting 3-nitro-N-(RCO)-4-(Py-Y)-benzeneamine with hydrogen under catalytic hydrogen conditions.

18 Claims, No Drawings

5-(PYRIDINYL)-1H-BENZIMIDAZOLES AND 1-HYDROXY-6-(PYRIDINYL)-1H-BENZIMIDAZOLES AND THEIR CARDIOTONIC USE

CROSS-REFERENCE TO RELATED APPLICATION

An intermediate disclosed herein, namely, 4-(3,4-diaminophenyl)pyridine or salt thereof, its preparation and its use as a cardiotonic agent are disclosed and claimed in copending application Ser. No. 173,003, filed July 28, 1980, now U.S. Pat. No. 4,297,362 issued Oct. 27, 1981 a continuation-in-part of application Ser. No. 40,210, filed May 18, 1979 and now abandoned.

BACKGROUND OF THE INVENTION (a) Field of the invention

This invention relates to (pyridinyl)-Y-benzimidazoles, their preparation and their use as cardiotonic agents, where Y is a direct linkage or lower-alkylene.

(b) Description of the Prior Art

Zubarovakii et al. [(Inst. Org. Khim., Kiev, USSR) Khim. Geterotsikl. Soedin. 1972, (5), 687–90 (Russ.); C.A. 77, 141,468k (1972)], in a paper entitled "Synthesis of Benzimidazole Derivatives. V. Pyridylbenzimidazoles and Cyanine Dyes From Them" disclose, inter alia, the monohydrochloride of 2-methyl-5-(2-pyridinyl)-1H-benzimidazole, 1-ethyl-2-methyl-5-(2-pyridinyl)-1H-benzimidazole and 2-methyl-1-(2-pyridinyl)-1H-benzimidazole, all as intermediates for preparing cyanine dyes.

The abstract of Lauer and Walser U.S. Pat. No. 4,026,936, issued May 31, 1977, discloses "compounds represented by the formula

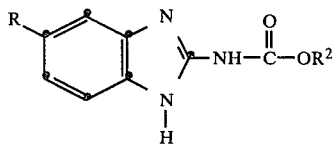

wherein R is

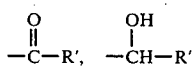

ps or —(CH$_2$)$_n$—R', R' is 2-pyridyl, 3-pyridyl, 4-pyridyl or 2-thiazyl, R$^2$ is lower alkyl and n is 1 or 2, and acid addition salts of the compounds wherein R' is 2-pyridyl, 3-pyridyl or 4-pyridyl are disclosed as useful as anthelmintics against a broad spectrum of helminths." Specifically disclosed as Example 36 (column 16, lines 47–67) is methyl [5(6)-2-pyridinylmethyl)-2-benzimidazolyl]-carbamate.

SUMMARY OF THE INVENTION

In a composition of matter aspect, the invention resides in 2-R-5-(Py-Y)-1H-benzimidazole or pharmaceutically-acceptable acid-addition salt thereof, useful as a cardiotonic agent, where R, Py and Y are defined hereinbelow.

A composition aspect of the invention resides in a cardiotonic composition for increasing cardiac contractility in a patient, said composition comprising a pharmaceutically-acceptable carrier and, as the active ingredient thereof, a cardiotonically-effective amount of 2-R-5-(Py-Y)-1H-benzimidazole or pharmaceutically-acceptable acid-addition salt thereof.

In a method aspect, the invention resides in a method for increasing cardiac contractility in a patient requiring such treatment which comprises the administration of a medicament comprising a pharmaceutically-acceptable carrier and, as the active component thereof, a cardiotonically-effective amount of 2-R-5-(Py-Y)-1H-benzimidazole or pharmaceutically-acceptable acid-addition salt thereof.

The invention is a process aspect comprises reacting 4-(Py-Y)-1,2-benzenediamine with R—C(OR$_1$)$_3$ to produce 2-R-5-(Py-Y)-1H-benzimidazole where R$_1$ is defined below.

The invention in another process aspect comprises reacting 4-(Py-Y)-1,2-benzenediamine with dimethylformamide dimethyl acetal or dimethylacetamide dimethyl acetal to produce 2-R-5-(Py-Y)-1H-benzimidazole where R is methyl or ethyl respectively.

Another process aspect of the invention comprises reacting 4-(Py-Y)-1,2-benzenediamine with an alkanoylating agent providing R'CO to produce N$_2$—[R'—C(=O)]-4-(Py-Y)-1,2-benzenediamine and heating the latter to produce 2-R'-5-(Py-Y)-1H-benzimidazole where R' is lower-alkyl.

Another composition of matter aspect of the invention resides in 1-hydroxy-2-R-6-(Py-Y)-1H-benzimidazole or pharmaceutically-acceptable acid-addition salt thereof, useful as a cardiotonic agent, where R, Py and Y are defined hereinbelow.

Another composition aspect of the invention resides in a cardiotonic composition for increasing cardiac contractility, said composition comprising a pharmaceutically-acceptable carrier and, as the active ingredient thereof, a cardiotonically-effective amount of 1-hydroxy-2-R-6-(Py-Y)-1H-benzimidazole or pharmaceutically-acceptable acid-addition salt thereof.

In another method aspect, the invention resides in a method for increasing cardiac contractility in a patient requiring such treatment which comprises the administration of a medicament comprising a pharmaceutically-acceptable carrier and, as the active component thereof, a cardiac cardiotonically-effective amount of 1-hydroxy-2-R-6-(Py-Y)-1H-benzimidazole or pharmaceutically-acceptable acid-addition salt thereof.

In another process aspect the invention resides in the process which comprises reacting 3-nitro-N-(RCO)-4-(PY-Y)-1-benzeneamine with hydrogen under catalytic hydrogen conditions to produce 1-hydroxy-2-R-6-(Py-Y)-1H-benzimidazole.

DETAILED DESCRIPTION INCLUSIVE OF PREFERRED EMBODIMENTS

In a composition of matter aspect the invention resides in a 2-R-5-(Py-Y)-1H-benzimidazole having formula I

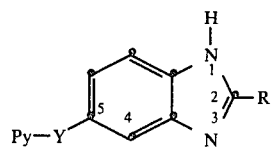

where Y is a direct linkage or lower-alkylene having one or two carbon atoms, R is hydrogen or lower-alkyl, and Py is 4- or 3-pyridinyl or 4- or 3-pyridinyl having one or two lower-alkyl substituents, or pharmaceutically-acceptable acid-addition salts thereof. The compounds of formula I are useful as cardiotonic agents, as determined by standard pharmacological evaluation procedures. Preferred embodiments are those of formula I where Py is 4-pyridinyl or 3-pyridinyl, Y is a direct linkage or methylene, and R is hydrogen, methyl or ethyl.

The compound of formula I may exist in tautomeric forms, that is, as 2-R-5-(Py-Y)-1H-benzimidazole of formula I or as 2-R-6-(Py-Y)-1H-benzimidazole of formula IA, illustrated as follows

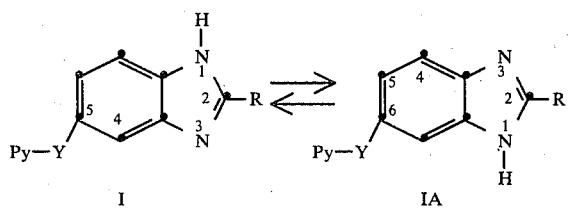

Although in the instant application we have preferred to use the names based on structure I, it is understood that either one or both of the structures I and IA are comprehended herein.

A composition aspect of the invention resides in a cardiotonic composition for increasing cardiac contractility, said composition comprising a pharmaceutically-acceptable carrier and, as the active component thereof, a cardiotonically-effective amount of 2-R-5-(Py-Y)-1H-benzimidazole of formula I where Py, Y and R are each defined as in formula I, or pharmaceutically-acceptable acid-addition salt thereof. Preferred embodiments are those having as active components the above-said preferred embodiments of formula I.

A method aspect of the invention resides in the method for increasing cardiac contractility in a patient requiring such treatment which comprises administering orally or parenterally in a solid or liquid dosage form to such patient a medicament comprising a pharmaceutically-acceptable carrier and, as the active component thereof, a cardiotonically-effective amount of 2-R-5-(Py-Y)-1H-benzimidazole of formula I where Py, Y and R are each defined as in formula I, or pharmaceutically-acceptable acid-addition salt thereof. Preferred embodiments are those using as active components the preferred embodiments of formula I.

In a process aspect the invention resides in the process which comprises reacting 4-(Py-Y)-1,2-benzenediamine with a tri-(lower-alkyl) ortho(lower-alkanoate) of the formula $R-C(OR_1)_3$ to produce 2-R-5-(Py-Y)-1H-benzimidazole where R, Y and Py are defined as above in formula I and $R_1$ is lower-alkyl. Preferred embodiments of this process aspect are those which produce said preferred composition of matter aspects of formula I where R is hydrogen and where $R_1$ is ethyl.

The invention in another process aspect comprises reacting 4-(Py-Y)-1,2-benzenediamine with dimethylformamide dimethyl acetal or dimethylacetamide dimethyl acetal to produce 2-R-5-(Py-Y)-1H-benzimidazole where R is hydrogen or methyl respectively, and Py and Y are defined as above in formula I. Preferred embodiments of this process aspect are those which produce said preferred composition of matter aspects of formula I where R is hydrogen or methyl.

Another process aspect of the invention comprises reacting 4-(Py-Y)-1,2-benzenediamine with one molar equivalent quantity of an alkanoylating agent providing alkanoyl of the formula

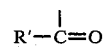

to produce $N_2-[R'-C(=O)]-4-(Py-Y)-1,2$-benzenediamine and heating the latter compound to produce 2-R'-5-(Py-Y)-1H-benzimidazole where Py and Y are defined as in formula I and R' is lower-alkyl. Preferred embodiments of this process aspect are those which produce said preferred composition of matter aspects of formula I.

Another composition of matter aspect of the invention resides in 1-hydroxy-2-R-6(Py-Y)-1H-benzimidazole having formula II

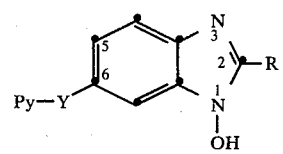

where Y is a direct linkage or lower-alkylene having one or two carbon atoms, R is hydrogen or lower-alkyl, and Py is 4- or 3-pyridinyl or 4- or 3-pyridinyl having one or two lower-alkyl substituents, or pharmaceutically-acceptable acid-addition salts thereof. The compounds of formula II are useful as cardiotonic agents, as determined by standard pharmacological evaluation procedures. Preferred embodiments are those of formula II where Py is 4-pyridinyl or 3-pyridinyl Y is a direct linkage or methylene, and R is hydrogen, methyl or ethyl.

Another composition aspect of the invention resides in a cardiotonic composition for increasing cardiac contractility, said composition comprising a pharmaceutically-acceptable carrier and, as the active component thereof, a cardiotonically-effective amount of 1-hydroxy-2-R-6-(Py-Y)-1H-benzimidazole of formula I where Py, and R are each defined as in formula I, or pharmaceutically-acceptable acid-addition salt thereof. Preferred embodiments are those having as active components the above-said preferred embodiments of formula II.

Another method aspect of the invention resides in the method for increasing cardiac contractility in a patient requiring such treatment which comprises administering orally or parenterally in a solid or liquid dosage form to such patient a medicament comprising a pharmaceutically-acceptable carrier and, as the active component thereof, a cardiotonically-effective amount of 1-hydroxy-2-R-6-(Py-Y)-1H-benzimidazole of formula II where Py, Y and R are each defined as in formula II, or pharmaceutically-acceptable acid-addition salt thereof. Preferred embodiments are those using as active components the preferred embodiments of formula II.

In another process aspect the invention resides in the process which comprises reacting 2-nitro-N-(RCO)-4-(Py-Y)-1-benzeneamine with hydrogen under catalytic hydrogenation conditions to produce 1-hydroxy-2-R-6-(Py-Y)-1H-benzimidazole. Preferred embodiments are those which produce the preferred embodiments of formula II.

The term "lower-alkyl" as used herein, e.g., as one of the meanings for R in formula I or as a substituent for Py in formula I or as R', means alkyl radicals having from one to six carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

Illustrative of Py in formula I where Py is 4- or 3-pyridinyl having one or two lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The term lower-alkylene as used herein, e.g., as one of the meanings for Y in formula I means lower-alkylene radicals having one or two carbon atoms, illustrated by —CH$_2$—, —CH$_2$CH$_2$— or

—CH(CH$_3$).

The compounds of formula I or II are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salt whose anions are relatively innocuous to the animal organism in pharmaceutical doses of the salts, so that the beneficial cardiotonic properties inherent in the free base (I or II) are not vitiated by side effects ascribable to the anions. In practicing the invention, it is convenient to use the free base form and the methanesulfonate salt; however, appropriate pharmaceutically-acceptable salts within the scope of the invention are those derived from other mineral acids such as hydrochloric acid, hydrobromic acid, sulfuric acid, phosphoric acid and sulfamic acid; and organic acids such as acetic acid, citric acid, lactic acid, tartaric acid, ethanesulfonic acid, benzenesulfonic acid, p-toluenesulfonic acid, cyclohexylsulfamic acid, quinic acid, and the like, giving the hydrochloride, hydrobromide, sulfate, phosphate, sulfamate, acetate, citrate, lactate, tartrate, ethanesulfonate, benzenesulfonate, cyclohexylsulfamate and quinate, respectively.

The acid-addition salts of said basic compound (I or II) are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound (I or II) are preferred, all acid-addition salts are within the scope of the invention. All acid-addition salts are useful as sources of the free base form even if the particular salt per se is desired only as an intermediate product as for example when the salt is formed only for purposes of purification or identification, or when it is used an an intermediate in preparing a pharmaceutically-acceptable salt by ion exchange procedures.

The molecular structure of the compound of formula I or II was assigned on the basis of evidence provided by infrared, nuclear magnetic resonance and mass spectra, and by the correspondence of calculated and found values for the elementary analysis.

The manner of making and using the instant invention will now be generally described so as to enable a person skilled in the art of pharmaceutical chemistry to make and use the same, as follows.

The preparation of 2-R-5-(Py-Y)-1H-benzimidazole by reacting 4-(Py-Y)-1,2-benzenediamine with R—C-(OR$_1$)$_3$ is conveniently and preferably carried out by heating the reactants at about 50° C. to 100° C., preferably about 60° C. to 80° C., in the absence or presence of a suitable solvent, e.g., a lower-alkanol, preferably ethanol; other solvents include dimethylformamide, p-dioxane, toluene, and the like. Similarily the preparation of 2-(methyl or ethyl)-5-(Py-Y)-1H-benzimidazole by reacting 4-(Py-Y)-1,2-benzenediamine respectively with dimethylformamide dimethyl acetal or with dimethylacetamide dimethyl acetal is carried out by heating the reactants at about 50° C. to 100° C., preferably at about 60° C. to 80° C., in the absence or presence of a suitable solvent, e.g., dimethylformamide, acetonitrile, p-dioxane, and the like.

The reaction of 4-(Py-Y)-1,2-benzenediamine with an alkanoylating agent providing alkanoyl of the formula

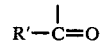
R'—C=O to produce N$_2$—[R'—C(=O)]-4-(Py-Y)-1,2-benzenediamine is carried out by reacting said 1,2-benzenediamine with one molar equivalent quantity of an alkanoylating agnet, preferably an alkanoyl acid halide of the formula R'—C(=O)-halide or alkanoic acid anhydride of the formula (R'CO)$_2$O.

N$_2$—[R'—C(=O)]-4-(Py-Y)-1,2-benzenediamine is conveniently converted into 2-R'-5-(Py-Y)-1H-benzimidazole by heating it in the absence or presence of a suitable solvent, e.g., dimethylformamide, dimethyl sulfoxide, at about 150° C. to 200° C.

The preparation of 1-hydroxy-2-R-6-(Py-Y)-1H-benzimidazole is carried out by reacting 3-nitro-N-(RCO)-4-(Py-Y)-1-benzeneamine with hydrogen preferably in a suitable solvent, e.g., acetic acid, ethanol, under catalytic hydrogenation conditions using a suitable hydrogenation catalyst, e.g., platinum oxide, palladium-on-charcoal.

The following examples with further illustrate the invention without, however, limiting it thereto.

A. 4-(Py-Y-)-1,2-benzenediamines

A-1. 4-(4-Pyridinyl)-1,2-benzenediamine—A mixture containing 115 g. of 4-(4-amino-3-nitrophenyl)pyridine, 1100 ml. of acetic acid and 1.2 g. of platinum oxide was shaken at room temperature under hydrogen under catalytic hydrogenation conditions until the required amount (1.5 mole) of hydrogen was taken up. The catalyst was filtered off and the filtrate concentrated in vacuo under reduced pressure. The residue was titrated with aqueous ammonium hydroxide to liberate the free base form of the product which was recrystallized from ethanol to yield 50.4 g. of 4-(4-pyridinyl)-1,2-benzenediamine, m.p. 260°–267° C. with decomposition.

A-2. 4-(4-Pyridinyl)-1,2-benzenediamine—A mixture containing 8 g. of 4-(4-acetylamino-3-nitrophenyl)-pyridine, 40 ml. of concentrated hydrochloric acid, 15 ml. of ethanol and 27 g. of stannous chloride dihydrate was stirred for 30 minutes at room temperature and then heated on a steam bath for four hours. The reaction mixture was cooled in an ice bath and the separated solid was collected. The solid was suspended in water and the mixture was basic by adding 35% aqueous sodium hydroxide solution. The yellow solid precipitate was collected, washed with water and dried to yield 3.60 g. of 4-(4-pyridinyl)-1,2-benzenediamine, m.p. 255°–258° C. A mixed melting point of this compound and the product obtained above in Example A-1 showed no depression.

A-3. 4-(4-Pyridinyl)-1,2-benzenediamine—To a stirred solution containing 27 g. of stannous dichloride dihydrate, 40 ml. of concentrated hydrochloric acid and 15 ml. of ethanol was added 7.2 g. of 4-(3-acetylamino-4-nitrophenyl)pyridine and the resulting mixture was stirred while heating on a steam bath for two hours and then allowed to stand at room temperature overnight (about fifteen hours). The solid was collected and then treated with 35% aqueous sodium hydroxide solution with stirring for about fifteen minutes. The yellow solid was collected from the resulting mixture to yield 3.4 g. of 4-(3,4-diaminophenyl)pyridine, m.p. 245°–250.3° C. The mass spectral data of this compound obtained by the above procedure is consistent with that of 4-(4-pyridinyl)-1,2-benzenediamine.

The above intermediate 4-(3-acetylamino-4-nitrophenyl)pyridine was prepared by the following procedure: To 65 ml. of ice cold 90% HNO$_3$ was added slowly with stirring 16.5 g. of 3-(4-pyridinyl)acetanilide so that the temperature of the reaction mixture did not rise above 5° C. The reaction mixture was maintained below this temperature for six hours and then poured into ice cold water. The resulting mixture was made basic with ammonium hydroxide and the mixture then acidified with acetic acid. The resulting light yellow solid was collected, washed with water, dried and crystallized from ethanol to produce 9.2 g. of 4-(3-acetylamino-4-nitrophenyl)pyridine, m.p. 175°–177° C.

A-4. 4-(2,6-Dimethyl-4-pyridinyl)-1,2-benzenediamine, 48.4 g. as its dimethanesulfonate, m.p. 255°–258° C., was prepared following the procedure described in Example A-1 using 34 g. of 4-(3-amino-4-nitrophenyl)-2,6-dimethyl pyridine, 200 ml. of acetic acid and 1 g. of platinum oxide, and converting the diamine base in isopropyl alcohol to its dimethanesulfonate with excess methanesulfonic acid.

4-(3-Amino-4-nitrophenyl)-2,6-dimethylpyridine was prepared in two steps by first nitrating (with 45 ml. of concentrated nitric acid) 10 g. of 3-(2,6-dimethyl-4-pyridinyl)acetanilide using the procedure given above in the second paragraph of Example A-3 to produce 5.2 g. of 4-(3-acetylamino-4-nitrophenyl)-2,6-dimethylpyridine and hydrolyzing the latter compound (41.2 g.) with 6 N aqueous hydrochloric acid to produce 4-(3-amino-4-nitrophenyl)-2,6-dimethylpyridine (34.2 g.), m.p. 226°–229° C.

Following the two step procedure described in Example A-3 but using in place of 3-(4-pyridinyl)acetanilide a molar equivalent quantity of the appropriate 3-(PY)acetanilide, it is contemplated that there can be obtained successively the corresponding 3(4 or 5)-(3-acetylamino-4-nitrophenyl)pyridines and 4-(Py)-1,2-benzenediamines respectively of Examples A-5 through A-11.

A-5. 3-(3-Acetylamino-4-nitrophenyl)pyridine and 4-(3-pyridinyl)-1,2-benzenediamine, using 3-(3-pyridinyl)acetanilide.

A-6. 4-(3-Acetylamino-4-nitrophenyl)-2-methylpyridine and 4-(2-methyl-4-pyridinyl)-1,2-benzenediamine, using 3-(2-methyl-4-pyridinyl)acetanilide.

A-7. 5-(3-Acetylamino-4-nitrophenyl)-2-methylpyridine and 4-(2-methyl-5-pyridinyl)-1,2-benzenediamine, using 3-(2-methyl-5-pyridinyl)acetanilide.

A-8. 4-(3-Acetylamino-4-nitrophenyl)-2,6-diethylpyridine and 4-(2,6-diethyl-4-pyridinyl)-1,2-benzenediamine, using 3-(2,6-diethyl-4-pyridinyl)acetanilide.

A-9. 4-(3-Acetylamino-4-nitrophenyl)-2-ethylpyridine and 4-(2-ethyl-4-pyridinyl)-1,2-benzenediamine, using 3-(2-ethyl-4-pyridinyl)acetanilide.

A-10. 4-(3-Acetylamino-4-nitrophenyl)-2,3-dimethylpyridine and 4-(2,3-dimethyl-4-pyridinyl)-1,2-benzenediamine, using 3-(2,3-dimethyl-4-pyridinyl)acetanilide.

A-11. 4-[(4-Pyridinyl)methyl]-1,2-benzenediamine, m.p. 156°–158° C., 13.9 g. was obtained following the procedure described in Example A-1 using 20 g. of 4-[(4-amino-3-nitrophenyl)methyl]pyridine, 250 ml. of acetic acid and 0.40 g. of platinum oxide.

The above intermediate, 4-[(4-amino-3-nitrophenyl)methyl]pyridine was prepared in several steps as follows: Two portions, 25 g. and 15.26 g. of 4-(4-nitrobenzyl)pyridine were catalytically hydrogenated (75 and 45 minutes respectively) at room temperature using in each instance 250 ml. of acetic acid and 0.40 g. of platinum oxide, filtering off the catalyst in each, combining the filtrates, concentrating in vacuo, dissolving the residue in water, making the aqueous solution alkaline with ammonium hydroxide, collecting the precipitate, recrystallizing the solid from isopropyl alcohol (final volume of 100 ml. and drying the recrystallized material in vacuo at 70° C. for 60 hours to yield 26.5 g. of 4-[(4-aminophenyl)methyl]pyridine, m.p. 157.5°–159° C., which was acetylated using 80 ml. of acetic anhydride and 160 ml. of chloroform to produce 25 g. of 4-[(4-acetylaminophenyl)methyl]pyridine, m.p. 172°–173.5° C., in turn, nitrated as above (second paragraph of Example A-3) using 120 ml. of 90% nitric acid and recrystallizing the nitrated product with isopropyl alcohol-water to produce 17.64 g. of 4-[(4-acetylamino-3-nitrophenyl)methyl]pyridine, m.p. 156°–157.5° C. 4-[(4-Amino-3-nitrophenyl)methyl]pyridine, m.p. 150°–151.5° C., 14.1 g., was obtained by refluxing with stirring for three hours a mixture containing 16.9 g. of 4-[(4-acetylamino-3-nitrophenyl)methyl]pyridine, 17.3 g. of potassium hydroxide, 270 ml. of ethanol and 110 ml. of water, chilling the reaction mixture, collecting the precipitated product and drying it at 90° C. for more than six hours. Then, following the procedure described above in Example A-1 using 20 g. of 4-[(4-amino-3-nitrophenyl)methyl]pyridine, 250 ml. of acetic acid and 0.40 g. of platinum oxide, there was obtained 13.9 g. of 4-[(4-pyridinyl)methyl]-1,2-benzenediamine, m.p. 156°–158° C.

B. 2-R-5-(Py-Y)-1H-benzimidazoles

B-1. 5-(4-Pyridinyl)-1H-benzimidazole—A mixture containing 4 g. of 4-(4-pyridinyl)-1,2-benzenediamine, 30 ml. of ethanol and 3.5 ml. of triethyl orthoformate was refluxed with stirring for eight hours and then evaporated to dryness in vacuo. The solid residue was dissolved in ethanol, the ethanol solution was treated with excess methanesulfonic acid and the separated precipitate was collected and dried at 70° C. to produce 6.2 g. of 5-(4-pyridinyl)-1H-benzimidazole as its dimethanesulfonate, m.p. 233°–235° C.

Other acid-addition salts of 5-(4-pyridinyl)-1H-benzimidazole are conveniently prepared by adding to a mixture of 2 g. of 5-(4-pyridinyl)-1H-benzimidazole in about 40 ml. of aqueous methanol the appropriate acid, e.g., concentrated sulfuric acid, concentrated phosphoric acid, to a pH of about 2 to 3, chilling the mixture after partial evaporation and collecting the precipitated salt, e.g., sulfate, phosphate, respectively. Also, the acid-addition salt is conveniently prepared in aqueous solution by adding to water with stirring molar equivalent quantities each of 5-(4-pyridinyl)-1H-benzimidazole and the appropriate acid, e.g., lactic acid or hydrochloric acid, to prepare respectively the monolactate or monohydrochloride salt in aqueous solution.

B-2. 5-(2,6-Dimethyl-4-pyridinyl)-1H-benzimidazole as its dimethanesulfonate, m.p. 262°–264° C., 10.8 g., was prepared following the procedure described in Example B-1 using 10 g. of 4(2,6-dimethyl-4-pyridinyl)-1,2-benzenediamine, 100 ml. of ethanol, 12 ml. of triethyl orthoformate, a refluxing period of seven hours and crystallization of the product as its dimethanesulfonate from isopropyl alcohol.

B-3. 2-Methyl-5-(4-pyridinyl)-1H-benzimidazole as its dimethanesulfonate, m.p. 226°–228° C., 21.5 g., was prepared following the procedure described in Example B-1 using 11.8 g. of 4-(4-pyridinyl)-1,2-benzenediamine, 100 ml. of ethanol, 20 ml. of triethyl orthoacetate, a refluxing period of twenty-four hours, washing the product with water and recrystallization of the product as its dimethanesulfonate from isopropyl alcohol.

B-4. 2-Ethyl-5-(4-pyridinyl)-1H-benzimidazole, as its dimethanesulfonate, m.p. 182°–184° C., 24.7 g. was prepared following the procedure described in Example B-1 using 12 g. of 4-(4-pyridinyl)-1,2-benzenediamine, 100 ml. of ethanol, 20 ml. of triethyl orthopropionate, a reflux period of six hours, washing the product with 50% ether-methanol and recrystallization of the product as its dimethanesulfonate from isopropyl alcohol.

Following the procedure described in Example B-1 but using in place of 4-(4-pyridinyl-1,2-benzenediamine a molar equivalent quantities of the appropriate 4-(Py-Y)-1,2-benzenediamine and tri-(lower-alkyl) orthoalkanoate it is contemplated that there can be obtained respectively the corresponding 5-(Py-Y)-1H-benzimidazoles of Examples B-5 thru B-12.

B-5. 5-(3-Pyridinyl)-1H-benzimidazole—using 4-(3-pyridinyl)-1,2-benzenediamine and triethyl orthoformate.

B-6. 2-Ethyl-5-(2-methyl-4-pyridinyl)-1H-benzimidazole—using 4-(2-methyl-4-pyridinyl)-1,2-benzenediamine and triethyl orthopropionate.

B-7. 2-Methyl-5-(2-methyl-5-pyridinyl)-1H-benzimidazole—using 4-(2-methyl-5-pyridinyl)-1,2-benzenediamine and triethyl orthoacetate.

B-8. 5-(2,6-Dimethyl-4-pyridinyl)-1H-benzimidazole—using 4-(2,6-dimethyl-4-pyridinyl)-1,2-benzenediamine and triethyl orthoformate.

B-9. 2-n-Propyl-5-(2,6-diethyl-4-pyridinyl)-1H-benzimidazole—using 4-(2,6-diethyl-4-pyridinyl)-1,2-benzenediamine and triethyl orthobutyrate.

B-10. 2-n-Amyl-5-(2-ethyl-4-pyridinyl)-1H-benzimidazole—using 4-(2-ethyl-4-pyridinyl)-1,2-benzenediamine and triethyl orthocaproate.

B-11. 2-Ethyl-5-[(4-pyridinyl)methyl]-1H-benzimidazole—using 4-[(4-pyridinyl)methyl]-1,2-benzenediamine and triethyl orthopropionate.

B-12. 2-Methyl-5-(2,3-dimethyl-4-pyridinyl)-1H-benzimidazole—using 4-(2,3-dimethyl-4-pyridinyl)-1,2-benzenediamine and triethyl orthoacetate.

Following the procedure described in Examples B-1 but using in place of triethyl orthoformate a molar equivalent quantity of dimethylformamide dimethyl acetal or dimethylacetamide dimethyl acetal and using dimethylformamide as solvent in place of ethanol, it is contemplated that there can be obtained the corresponding respective products of Examples B-1 and B-3, namely, 5-(4-pyridinyl)-1H-benzimidazole and 2-methyl-5-(4-pyridinyl)-1H-benzimidazole. Also, it is contemplated that 2-methyl-5-(4-pyridinyl)-1H-benzimidazole can be obtained by refluxing $N_2$-acetyl-4-(4-pyridinyl)-1,2-benzenediamine in dimethylformamide, cooling the reaction mixture and collecting said product by filtration.

C. 1-Hydroxy-2-R-6-(Py-Y)-1H-benzimidazoles

C-1. 1-Hydroxy-2-methyl-6-(4-pyridinyl)-1H-benzimidazole—A mixture containing 12.9 g. 4-(4-acetylamino-3-nitrophenyl)pyridine, 150 ml. of acetic acid and 500 mg. of platinum oxide was agitated under hydrogen under catalytic hydrogenation conditions until the required amount of hydrogen was teken up. The catalyst was filtered off; the filtrate was concentrated; 50 ml. of concentrated hydrochloric acid was added; and, the mixture was refluxed for seven hours. The reaction mixture was concentrated, neutralized by adding ammonium hydroxide, and then reacidified with acetic acid and chilled. The separated solid was collected, dissolved in hot ethanol and methanesulfonic acid, the solution allowed to cool and the precipitate collected and dried at 70° C. to yield 10.3 g. of 1-hydroxy-2-methyl-6-(4-pyridyl)-1H-benzimidazole dimethanesulfonate, m.p. 219°–220° C.

Other acid-addition salts of 1-hydroxy-2-methyl-6-(4-pyridinyl)-1H-benzimidazole are conveniently prepared by adding to a mixture of 2 g. of 1-hydroxy-2-methyl-6-(4-pyridinyl)-1H-benzimidazole in about 40 ml. of aqueous methanol and appropriate acid, e.g., concentrated sulfuric acid, concentrated phosphoric acid, to a pH of about 2 to 3, chilling the mixture after partial evaporation and collecting the precipitated salt, e.g., sulfate, phosphate, respectively. Also, the acid-addition salt is conveniently prepared in aqueous solution by adding to water with stirring molar equivalent quantities each of 1-hydroxy-2-methyl-6-(4-pyridinyl)-1H-benzimidazole and the appropriate acid, e.g., lactic acid or hydrochloric acid, to prepare respectively the monolactate or monohydrochloride salt in aqueous solution.

C-2. 1-Hydroxy-6-(4-pyridinyl)-1H-benzimidazole—A mixture containing 26 g. of a mixture of 4-(4-formylamino-3-nitrophenyl)pyridine and 4-(4-acetylamino-3-nitrophenyl)pyridine (preparation given below), 200 ml. of acetic acid and 1 g. of platinum oxide was agitated under hydrogen under catalytic hydrogenation conditions until there was no further uptake of hydrogen. The catalyst was filtered off, the filtrate was concentrated in vacuo and the residue was dissolved in water. The aqueous solution was made basic by adding ammonium hydroxide. When the separated oily material failed to solidify, 100 ml. of concentrated hydrochloric acid was added to the mixture and the resulting dark solution was evaporated to dryness in vacuo. The remaining solid was dissolved in water and the solution made basic by adding aqueous potassium carbonate solution. The yellow solid that separated was collected, dried at 70° C., and recrystallized from ethanol to produce 4.4 g. of 1-hydroxy-6-(4-pyridinyl)-1H-benzimidazole, m.p. 186°–188° C.

The above intermediate mixture of 4-(4-formylamino-3-nitrophenyl)pyridine and 4-(4-acetylamino-3-nitrophenyl)pyridine was prepared in two steps as follows: To a stirred ice cold mixture containing 34 g. of 4-(4-pyridinyl)benzeneamine, 400 ml. of chloroform and 10.2 g. (8.7 ml.) of 97% formic acid was added slowly 23 g. (22.5 ml.) of acetic anhydride over a two hour period. The resulting red solution was allowed to stand at room temperature overnight and the chloroform was then distilled off in vacuo. The residual red oil was poured into a solution of aqueous potassium carbonate solution. The pale orange solid was collected and dried at 70° C. to produce 23.4 g. of a 70:30 (wt./wt.) mixture (as indicated by its n.m.r. spectrum) of 4-(4-acetylaminophenyl)pyridine and 4-(4-formylaminophenyl)pyridine. This mixture of compounds (23.4 g.) was then added with stirring over a forty minute period to 100 ml. of ice cold concentrated nitric acid keeping the temperature below 10° C. The reaction mixture was stirred further for one hour and then poured into ice cold water. The aqueous mixture was made basic by adding potassium carbonate. The resulting yellow solid was collected, washed with water and dried at 70° C. to yield 27.4 g. of a mixture of 4-(4-acetylamino-3-nitrophenyl)pyridine and 4-(4-formylamino-3-nitrophenyl)pyridine, m.p. 160°–200° C.

Following the above procedure using the generally known steps of first formylating and acetylating 4-(4-pyridinyl)-1-benzeneamine to produce the mixture of 4-(4-formylaminophenyl)pyridine and 4-(4-acetylaminophenyl)pyridine and then nitrating the latter mixture to form the mixture of corresponding 4-[4-formylamino (and 4-acetylamino)-3-nitrophenyl]pyridines but starting with a molar equivalent quantity the appropriate lower-alkanoylating agent (acid chloride or anhydride) in place of formic acid and acetic anhydride, it is contemplated that the following intermediate 4-[(4-(lower-alkanoylamino)-3-nitrophenyl)]pyridines can be prepared: 4-(4-propionylamino-3-nitrophenyl)pyridine, 4-(4-butyrylamino-3-nitrophenyl)pyridine and 4-(4-caproylamino-3-nitrophenyl)pyridine.

Following the procedure described in Example C-1 using in place 4-(4-acetylamino-3-nitrophenyl)pyridine a molar equivalent quantity of the appropriate 4 (or 3)-[(4-(lower-alkanoylamino)-3-nitrophenyl]pyridine, it is contemplated that the corresponding 1-hydroxy-2-R-6-PY-1H-benzimidazoles of Example C-3 through C-9 can be obtained.

C-3. 1-Hydroxy-2-ethyl-6-(4-pyridinyl)-1H-benzimidazole—using 4-(4-propionylamino-3-nitrophenyl)-pyridine.

C-4. 1-Hydroxy-2-n-propyl-6-(4-pyridinyl)-1H-benzimidazole—using 4-(4-butyrylamino-3-nitrophenyl)-pyridine.

C-5. 1-Hydroxy-2-n-amyl-6-(4-pyridinyl)-1H-benzimidazole—using 4-(4-caproylamino-3-nitrophenyl)-pyridine.

C-6. 1-Hydroxy-2-methyl-6-[(4-pyridinyl)methyl]-1H-benzimidazole—using 4-[(4-acetylamino-3-nitrophenyl)methyl]pyridine.

C-7. 1-Hydroxy-2-methyl-6-(3-pyridinyl)-1H-benzimidazole—using 3-(4-acetylamino-3-nitrophenyl)-pyridine.

C-8. 1-Hydroxy-2-methyl-6-(2-methyl-4-pyridinyl)-1H-benzimidazole—using 4-(4-acetylamino-3-nitrophenyl)-2-methylpyridine.

C-9. 1-Hydroxy-2-methyl-6-(2,6-dimethyl-4-pyridinyl)-1H-benzimidazole—using 4-(4-acetylamino-3-nitrophenyl)-2,6-dimethylpyridine.

The usefulness of the compounds of formula I or II or salts thereof as cardiotonic agent is demonstrated by their effectiveness in standard pharmacological test procedures, for example, in causing a significant increase in contractile force of the isolated cat atria and papillary muscle and/or in causing a significant increase in the cardiac contractile for in the anesthetized dog with low or minimal changes in heart rate and blood pressure. Detailed descriptions of these test procedures appear in U.S. Pat. No. 4,072,746, issued Feb. 7, 1980.

When tested by said isolated cat atria and papillary muscle procedure, the compounds of formula I or II or pharmaceutically-acceptable acid-addition salts thereof at doses of 3, 10, 30, and/or 100 μg./ml., were found to cause significant increases, that is, greater than 25% in papillary muscle force and significant increases, that is, greater than 25%, in right atrial force, while causing a lower percentage increase (about one-half or less than the percentage increase in right atrial force or papillary muscle force) in right atrial rate. For example, when tested at said dose levels by this procedure, the following preferred compounds were found to cause increases of 29 to 228% in papillary muscle force and/or right atrial force: the compounds of Examples B-1, B-2, B-3, B-4, C-1 and C-2 the latter two being active at only 100 μg./ml.

When tested by said anesthetized dog procedure, the compounds of formula I or II or pharmaceutically-acceptable acid-addition salts thereof at doses of 1.0, 3.0 and/or 10 mg./kg. administered intravenously were found to cause significant increases, that is, 25% or greater, in cardiac contractile force or cardiac contractility with lower changes in heart rate and blood pressure. For example, when tested at one or more of said dose levels by this procedure, the following compounds were found to cause increases of 31 to 137% in contractile force and lower changes in heart rate and blood pressure: the compounds of Examples B-1, B-3, C-1 and C-2.

When screened by other standard pharmacological test procedures, some embodiments of the compounds of formula I or salts were found to have bronchodilator properties. For example, when tested orally at 100 mg./kg., the compounds of Examples B-1, B-2, B-3 and B-4 were each found to have bonchodilator activity by inhibiting bronchoconstriction induced by histamine, acetylcholine or immune complex in guinea pigs.

The present invention includes within its scope a cardiotonic composition for increasing cardiac contractility, said composition comprising a pharmaceutically-acceptable carrier and, as the active component thereof, a cardiotonically-effective amount of the compound of formula I or II or pharmaceutically-acceptable acid-addition salt thereof. The invention also includes within its scope the method for increasing cardiac contractility in a patient requiring such treatment which comprises administering to such patient a cardiotonically-effective amount of said compound of formula I or II or pharmaceutically-acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentages of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. 2-R-5-(Py-Y)-1H-benzimidazole having the formula

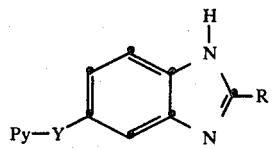

where Y is a direct linkage or lower-alkylene having one or two carbon atoms, R is hydrogen or lower-alkyl, and Py is 4- or 3-pyridinyl or 4- or 3-pyridinyl having one or two lower-alkyl substituents, or a pharmaceutically-acceptable acid-addition salt thereof.

2. A compound according to claim 1 where Py is 4- or 3-pyridinyl, Y is a direct linkage or methylene, and R is hydrogen, methyl or ethyl.

3. 5-(4-Pyridinyl)-1H-benzimidazole according to claim 2.

4. 5-(2,6-Dimethyl-4-pyridinyl)-1H-benzimidazole according to claim 1.

5. 2-Methyl-5-(4-pyridinyl)-1H-benzimidazole according to claim 2.

6. 2-Ethyl-5-(4-pyridinyl)-1H-benzimidazole according to claim 2.

7. A cardiotonic composition for increasing cardiac contractility, said composition comprising a pharmaceutically-acceptable inert carrier and, as the active component thereof, a cardiotonically-effective amount of 2-R-5-(Py-Y)-1H-benzimidazole or a pharmaceutically-acceptable acid-addition salt thereof, where Y is a direct linkage or lower-alkylene having one or two carbon atoms, R is hydrogen or lower-alkyl, and Py is 4- or 3-pyridinyl or 4- or 3-pyridinyl having one or two lower-alkyl substituents.

8. A composition according to claim 7 where Py is 4- or 3-pyridinyl, Y is a direct linkage or methylene, and R is hydrogen, methyl or ethyl.

9. The method for increasing cardiac contractility in a patient requiring such treatment which comprises administering to such patient a cardiotonically-effective amount of 2-R-5-(Py-Y)-1H-benzimidazole or a pharmaceutically-acceptable acid-addition salt thereof, where Y is a direct linkage or lower-alkylene having one or two carbon atoms, R is hydrogen or lower-alkyl, and Py is 4- or 3-pyridinyl or 4- or 3-pyridinyl having one or two lower-alkyl substituents.

10. The method according to claim 9 where Py is 4- or 3-pyridinyl, Y is a direct linkage or methylene, and R is hydrogen, methyl or ethyl.

11. 1-Hydroxy-2-R-6-(Py-Y)-1H-benzimidazole having the formula

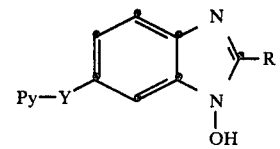

where Y is a direct linkage or lower-alkylene having one or two carbon atoms, R is hydrogen or lower-alkyl, and Py is 4- or 3-pyridinyl or 4- or 3-pyridinyl having one or two lower-alkyl substituents, or a pharmaceutically-acceptable acid-addition salt thereof.

12. A compound according to claim 11 where Py is 4- or 3-pyridinyl, Y is a direct linkage or methylene, and R is hydrogen, methyl or ethyl.

13. 1-Hydroxy-6-(4-pyridinyl)-1H-benzimidazole according to claim 12.

14. 1-Hydroxy-2-methyl-6-(4-Pyridinyl)-1H-benzimidazole according to claim 12.

15. A cardiotonic composition for increasing cardiac contractility, said composition comprising a pharmaceutically-acceptable inert carrier and, as the active component thereof, cardiotonically-effective amount of 1-hydroxy-2-R-6-(Py-Y)-1H-benzimidazole or a pharmaceutically-acceptable acid-addition salt thereof, where Y is a direct linkage or lower-alkylene having one or two carbon atoms, R is hydrogen or lower-alkyl, and Py is 4- or 3-pyridinyl or 4- or 3-pyridinyl having one or two lower-alkyl substituents.

16. A composition according to claim 15 where Py is 4- or 3-pyridinyl, Y is a direct linkage or methylene, and R is hydrogen, methyl or ethyl.

17. The method for increasing cardiac contractility in a patient requiring such treatment which comprises administering to such patient a cardiotonically-effective amount of 1-hydroxy-2-R-6-(Py-Y)-1H-benzimidazole or a pharmaceutically-acceptable acid-addition salt thereof, where Y is a direct linkage or lower-alkylene having one or two carbon atoms, R is hydrogen or lower-alkyl, and Py is 4- or 3-pyridinyl or 4- or 3-pyridinyl having one or two lower-alkyl substituents.

18. The method according to claim 17 where Py is 4- or 3-pyridinyl, Y is a direct linkage or methylene, and R is hydrogen, methyl or ethyl.

* * * * *

UNITED STATES PATENT AND TRADEMARK OFFICE
CERTIFICATE OF CORRECTION

PATENT NO. : 4,331,671
DATED : May 25, 1982
INVENTOR(S) : George Y. Lesher et al.

It is certified that error appears in the above-identified patent and that said Letters Patent are hereby corrected as shown below:

Column 1, line 49, delete "ps".

Column 2, line 11, "is" should read -- in --.

Column 6, line 39, "agnet" should read -- agent --.

Column 12, line 57, "bonchodilator" should read -- bronchodilator --.

Signed and Sealed this

First Day of February 1983

[SEAL]

Attest:

GERALD J. MOSSINGHOFF

Attesting Officer      Commissioner of Patents and Trademarks